United States Patent [19]

Virnig

[11] 4,210,759
[45] Jul. 1, 1980

[54] BENZENE SULFONAMIDO PYRIDINE DERIVATIVES

[75] Inventor: Michael J. Virnig, Fridley, Minn.

[73] Assignee: Henkel Corporation, Minneapolis, Minn.

[21] Appl. No.: 909,225

[22] Filed: May 24, 1978

[51] Int. Cl.² .............................................. C07D 213/42
[52] U.S. Cl. .................................... 546/312; 546/286; 546/289; 546/293; 546/334
[58] Field of Search ............... 546/312, 286, 289, 293, 546/334

[56] References Cited

U.S. PATENT DOCUMENTS

| | | | |
|---|---|---|---|
| 4,034,098 | 7/1977 | Archibald et al. | 546/312 |
| 4,148,901 | 4/1979 | Madsen et al. | 546/312 |

Primary Examiner—Alan L. Rotman
Attorney, Agent, or Firm—Patrick J. Span

[57] ABSTRACT

Certain sulfonamido pyridines, pyrimidines, benzothiazoles and oxazoles, metal complexes thereof and solutions of said compounds in essentially water-immiscible, liquid hydrocarbon solvents are disclosed. The sulfonamide compounds have the structural formula:

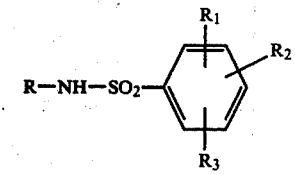

wherein $R$, $R_1$, $R_2$ and $R_3$ are as defined in the specification and claims hereof. Particular metal values are recovered from their aqueous solutions by using heterocyclic sulfonamide compounds dissolved in essentially water-immiscible, liquid hydrocarbon solvents. The extraction process generally comprises contacting the metal value containing aqueous solution with the solution of the sulfonamide compound in an essentially water-immiscible liquid hydrocarbon solvent and stripping the metal values from the loaded organic phase.

19 Claims, No Drawings

BENZENE SULFONAMIDO PYRIDINE DERIVATIVES

The present invention is directed to novel heterocyclic sulfonamide compounds, organic solvent solutions thereof, metal complexes of such compounds, organic solvent solutions of such complexes and the method of using said heterocyclic sulfonamide compounds to extract metal values from aqueous solution.

Liquid ion exchange recovery of metal values from aqueous solutions thereof has in the past ten years or so become a mature commercial operation. Such processing has been described as being deceptively simple since all that is really happening is the transfer of a metal value from Phase A (aqueous) to Phase B (organic) and thence from Phase B to Phase C (aqueous). However, complexities of liquid ion exchange arise in a number of areas including (1) synthesis and manufacture of the reagent system, (2) evaluation of the system's capabilities, and (3) engineering application leading to large scale metal recovery.

The key to a successful application of liquid ion exchange is the reagent. In this respect, the reagent should desirably meet a number of criteria. In the first instance, the reagent should complex with or react with a metal or group of metals and such complexing or reaction should be relatively fast in order to avoid having to use large holding tanks or reaction vessels. It is also desirable that the reagent exhibits preference for a single metal where the aqueous starting solutions contain a number of metal values. Such selectivity can often be optimized at designated pH ranges. The reagent should also desirably complex or react quantitatively with the metal under the extraction conditions. Additionally, the reagent, as well as the resulting metal complex, must exhibit satisfactory solubility in the essentially water-immiscible organic solvent being used. Further, the reagent-metal reaction or complexing should be reversible so that the metal can be stripped from the organic phase. For economic reasons, the reagent should be relatively stable so that it can be recycled repeatedly. Also, it should be essentially water insoluble to prevent significant loss into the aqueous phase or phases. Furthermore, the reagent should not cause or stabilize emulsions. Again and principally for economic reasons, the reagent should not react with or load significant quantities of acid, for example, from aqueous acidic stripping solutions. And, of course, the cost of the reagent should be such that the liquid ion exchange process can be operated at a profit.

Of significant, but lesser, importance, is the selection of the essentially water-immiscible solvent to be used in the liquid ion exchange process. Such selection is important principally from a cost standpoint, especially in the recovery of the more common metals. Existing commercial operations for copper recovery, for example, generally employ aliphatic kerosenes because of the low cost thereof. Thus the cost of the reagent and the solvent is intertwined in providing the desired overall economics of the process being commercialized.

One of the most extensively used systems in commercial operation in the last decade for copper recovery has employed benzophenoximes or combination reagents including a benzophenoxime component. While being economic, improvements can be made since the said benzophenoximes do not have total selectivity for copper over iron, for example. Other types of reagents which have been proposed for use in copper recovery such as the alkenyl substituted 8-hydroxyquinolines also have certain drawbacks.

More recently, novel sulfonamidoquinolines, particularly useful in liquid ion exchange metal recovery processes were discovered. These compounds and their use in liquid ion exchange metal recovery processes are the subject of commonly assigned co-pending applications Ser. Nos. 843,534 and 845,932. Another U.S. Pat. No. 3,133,945, to Billman and Chernin, relates to copper complexes of N-(2-amino-hydrocarbyl) sulfonamides. These applications further make reference to certain low molecular weight sulfonamidoquinolines as reported by Billman and Chernin in Analytical Chemistry, Vol. 34, No. 3, March 1962, pp. 408–410 and U.S. Pat. Nos. 3,268,538 and 3,337,555.

It has not been discovered that certain novel heterocyclic sulfonamide compounds, as more fully defined hereinafter, are useful in liquid ion exchange recovery processes. The new compounds of the present invention have the following structural formula:

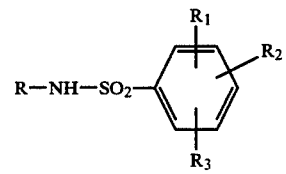

wherein R is a member selected from the group consisting of pyridine, pyrimidine, benzothiazole, isoxazole and phenyl benzoxazole, and $R_1$, $R_2$ and $R_3$, which may be the same or different, are selected from the group consisting of hydrogen, alkyl and alkenyl. When alkyl or alkenyl, $R_1$, $R_2$ and $R_3$ contain from 1 to 20 carbon atoms and, preferably, at least eight carbon atoms. Additionally, the alkyl and alkenyl groups may be linear or branched chain, although branched chain is preferred.

The compounds of the present invention are also characterized as having solubilities in essentially water-immiscible liquid hydrocarbon solvents of at least 2% by weight. Correspondingly, they are further characterized in that the copper ($Cu++$) complexes of the compound have solubilities of at least 2% by weight in the said water-immiscible, liquid hydrocarbon solvents. Especially preferred compounds of the invention are those which exhibit solubilities of at least 2% by weight in both pure and complexed form, in aliphatic or aromatic hydrocarbons, or mixtures thereof, having flash points of at least 150° F. Thus, the compounds of the invention may preferably be further characterized as having substituents containing a sufficient number of carbon atoms and/or branching in the alkyl and alkenyl groups to provide at least the minimum 2% solubility in the aforementioned solvents.

The preference for alkyl and alkenyl substituents containing at least 8 carbon atoms and/or possessing a branched chain structure is due to their contribution to the solubilities of the compounds in the above described solvents. The beneficial effect provided by the number of carbon atoms is obtained by having an alkyl or alkenyl substituent of at least 8 carbon atoms or more than one alkyl or alkenyl substituent in which the sum of the carbon atoms is at least 8. Accordingly, the most preferred compounds of the present invention are those possessing a branched chain alkyl or alkenyl substituent having at least 8 carbon atoms or those possessing branched chain alkyl or alkenyl substituents in which the sum of the carbon atoms is at least 8. Of the numerous compounds which exhibit these preferred characteristics, those in which one of $R_1$, $R_2$ and $R_3$ is dodecyl and those in which one of $R_1$, $R_2$ and $R_3$ is decyl and another is methyl have been found to be particularly effective in meeting the minimum solubility properties in the essentially water-immiscible, liquid hydrocarbon solvents.

The novel compounds of the present invention are generally represented by the structural formula:

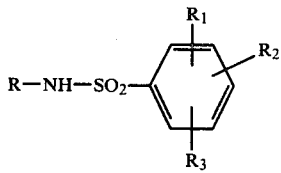

wherein $R_1$, $R_2$ and $R_3$ are as defined above, and R represents a heterocyclic structure. More particularly, R is a benzoxazole, pyridine, pyrimidine, benzothiazole or isoxazole group, and is bonded to the sulfonamido group through a carbon adjacent to one of the hetero atoms of the ring.

The benzothiazole group has the structural formula:

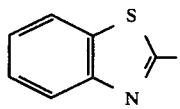

2-(Dodecylbenzenesulfonamido)benzothiazole is a preferred compound of the present invention as it exhibits good properties as a reagent for extracting metal values from aqueous solutions.

The isoxazole group, as contemplated by the present invention, has the structure:

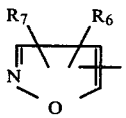

wherein $R_6$ and $R_7$, which may be the same or different, are selected from the group consisting of hydrogen and methyl. Of the various sulfonamido isoxazoles, 3,4-dimethyl-5-(dodecylbenzenesulfonamido)isoxazole and 2-(dodecylbenzenesulfonamido)5-methylisoxazole are preferred as metal ion extractants.

The benzoxazole group is a phenyl benzoxazole group having the structural formula:

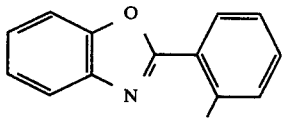

The preferred compound having this structure is 2-[2′(Decylmethylbenzenesulfonamido)phenyl]benzoxazole.

R may also represent a heterocyclic nitrogen group, i.e., pyrimidine and pyridine. The pyrimidine group is represented by the formula:

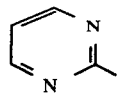

and the pyridine group has the structure:

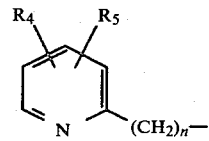

wherein $R_4$ and $R_5$, which may be the same or different, are selected from the group consisting of hydrogen, linear and branched chain alkyl and alkenyl containing from 1 to 20 carbon atoms, halogen, nitrile, trifluoromethyl and alkoxy containing from 1 to 20 carbon atoms and n is an integer equal to 0 or 1. Exemplary of the pyrimidine compounds are 2-(Dodecylbenzenesulfonamido)pyrimidine and 2-(Decylmethylbenzenesulfonamido)pyrimidine. Exemplary of the sulfonamido pyridines of the present invention are 2-(Dodecylbenzenesulfonamido)pyridine, 2-(Dodecylbenzensulfonamido)-6-methylpyridine, 3,5-Dichloro-2-(dodecylbenzenesulfonamido)pyridine, 2-(Dodecylbenzenesulfonamido)-3-methylpridine and 2-(Dodecylbenzenesulfonamidomethyl)pyridine.

The novel compounds of the present invention are prepared from the respective heterocyclic amines which have the general structural formula R—NH, wherein R is as defined above. The amine is dissolved in pyridine and alkyl or alkenyl substituted benzenesulfonyl chloride is added slowly with stirring. During this addition, the reaction temperature is maintained between 15° and 30° C. After the introduction of the sulfonyl chloride is complete, the reaction mixture is stirred at room temperature for a period of time ranging from 30 minutes to several hours. The reaction mixture is then heated to a temperature between 70° and 90° C. and stirred for a period of time ranging from 0.5 to 8 hours. Approximately 50 to 100 ml of water is added and the reaction mixture is stirred for 30 minutes at a temperature between 70° and 80° C. The reaction mixture is poured into approximately 250 to 1500 ml of water and the product is recovered by extraction with an organic solvent such as Skelly C, Skelly C/benzene (50:50) or pure benzene. After extraction, the organic extract is washed first with methanolic sodium bicarbonate and second with a 1 to 5% solution of a mineral acid, e.g., sulfuric or hydrochloric acid. The methanolic bicarbonate washes are repeated until clean phase separations are obtained. The organic phase is then washed with brine, dried over sodium sulfate, filtered and evaporated in vacuo to isolate the sulfonamido heterocyclic reaction product.

The starting materials for the preparation of the novel heterocyclic sulfonamide compounds may be prepared (if not commercially available) as follows. The starting amine may be prepared by amination of the corresponding pyridine, pyrimidine, benzothiazole, isoxazole and phenyl benzoxazole. The starting substituted benzenesulfonyl chlorides may be prepared from the corresponding alkylbenzene, alkylbenzenesulfonic acid, sodium sulfonate salt or alkyl halide, as described in commonly assigned co-pending applications Ser. Nos. 843,534 and 845,932, which disclosures are hereby incorporated by reference. Further details of the synthesis of the compounds of the invention, including information concerning the preparation of the various starting materials, are found in the Examples which follow the description of the invention.

It is generally difficult to prepare the sulfonamide compounds of the present invention having two large substituents on adjacent carbon atoms on the aromatic rings due to the problem of steric hindrance. Thus, it is preferred that the substituents represented by $R_1$, $R_2$ and $R_3$ are arranged on the benzene ring of the compounds of the present invention so as to be on non-adjacent carbon atoms. While this preferred embodiment facilitates preparation of the sulfonamide compounds of the invention, it does not affect the solubility of the compounds in the essentially water-immiscible, liquid hydrocarbon solvents or their ability to extract metal values from aqueous solutions. Thus, sulfonamide heterocyclic compounds with substituents on vicinal carbon atoms of the benzene rings are equally effective as extractants in the process of the invention, although they are more difficult to prepare.

The process of the present invention is a liquid ion exchange process in which any one of the heterocyclic sulfonamide compounds of the invention is dissolved in an essentially water-immiscible, liquid hydrocarbon solvent and the resulting solution is contacted with the metal containing aqueous phase to extract at least a portion of the metal values into the organic phase. The phases are then separated and metal values are stripped from the loaded organic phase by the use of an aqueous stripping medium.

A wide variety of essentially water-immiscible, liquid hydrocarbon solvents can be used in the metal recovery process of the present invention. These include: aliphatic and aromatic hydrocarbons such as kerosenes, benzene, toluene, xylene and the like. The choice of the said essentially water-immiscible liquid hydrocarbon solvent for particular commercial operations will depend on a number of factors including the design of the solvent extraction plant (i.e. mixer-settlers, Podbielniak extractors, etc.), the value of the metal being recovered, disposal of plant effluent and the like. The process of the present invention finds particular use in the extraction recovery of the major, non-ferrous, transition metals—i.e. copper, nickel, zinc, cobalt(II) and cobalt (III), as will be described more fully hereinbelow. Essentially, all of the major plants in operation currently for the recovery of these metal (particularly $Cu++$) use mixer-settlers with relatively large organic inventories and some loss of solvent invariably occurs by evaporation, entrainment in the aqueous and the like. Under these circumstances, preferred solvents for use in the metal recovery processes of the present invention are the aliphatic and aromatic hydrocarbons having flash points of 150° F. and higher and solubilities in water of less than 0.1% by weight. These solvents are also essentially non-toxic and chemically inert and the costs thereof are currently within practical ranges—i.e. normally less than one dollar (U.S.) per gallon to as low as 30¢ (U.S.) or so. Representative commercially available solvents are Kermac 470B (an aliphatic kerosene available from Kerr-McGee—Flash Point 175° F.), Chevron Ion Exchange Solvent (available from Standard Oil of California—Flash Point 195° 1 F.), Escaid 100 and 110 (available from Exxon-Europe—Flash Point≈180° F.), Norpar 12 (available from Exxon-U.S.A.—Flash Point 160° F.), Conoco C-1214 (available from Conoco—Flash Point 160° F.), Aromatic 150 (an aromatic kerosene available from Exxon-U.S.A.—Flash Point 150° F.) and various other kerosenes and petroleum fractions available from other oil companies.

The present invention thus additionally relates to new compositions wherein the sulfonamido compounds of the invention are dissolved in the essentially water-immiscible, liquid hydrocarbon solvents described above. In this regard, liquid ion exchange reagents are often sold as solutions in organic solvents. These new compositions consist essentially of solutions of at least 2% by weight of the sulfonamido compound in essentially water-immiscible, liquid hydrocarbon solvents. When sold as concentrates, the solutions will preferably contain from about 25 to 75% by weight of the sulfonamido product.

In the process of the present invention, the organic solvent solutions will preferably contain from about 2 to 75% by weight of the heterocyclic sulfonamide compounds and even more preferably from about 5 to 20% by weight thereof. Additionally, volume ratios of the organic:aqueous phase vary widely since the contacting of any quantity of the sulfonamide solution with the metal containing aqueous phase will result in extraction of metal values into the organic phase. However, for commercial practicality, the organic:aqueous phase ratios are preferably in the range of about 5:1 to 1:5. For practical purposes, the extracting and stripping are normally conducted at ambient temperatures and pressures although higher or lower temperatures and/or pressures are entirely operable. Most advantageously, the entire process can be carried out continuously with the stripped organic solvent solution being recycled for contacting further quantities of metal containing solutions.

The present invention also relates to the metal complexes of the novel sulfonamido compounds and to the essentially water-immiscible, liquid hydrocarbon solvent solutions thereof. The solutions consist essentially of the said solvent and at least 2% by weight, and preferably less than 75% by weight, of the metal complexes. While not normally practiced in the industry, the solutions of the metal complexes can be obtained at one location and transported to another for stripping as hereinafter described. The term "metal complex" as used herein is meant to connote compositions of the novel sulfonamido oximes with other than insignificant quantities of metal ions. Although the exact structural nature of these complexes has not been ascertained, indications are that under conditions of maximum loading, particularly with $Cu++$ and $Zn++$ metal ions, the complexes comprise the metal and sulfonamide compound generally in a molar ratio of 1:2. Maximum loading, however, is not required for achieving acceptable performance in liquid ion exchange processes and hence the metal complexes are generally defined as including the designated metals in more than insignificant quantities up to maximum loading.

The metal recovery process of the present invention is useful for the recovery of the following metal values from their aqueous solutions: $Cu++$, $Ni++$, $Zn++$, $Co++$ and $Co+++$. These metal values are all transition metals of Groups I b, II b and VIII. The extraction of these various metals from aqueous solutions depends upon a number of factors, including, for example, the concentration of the metal ion, the particular anions present, and the pH of and/or ammonia concentration in the aqueous solutions, as well as the particular sulfonamide compound chosen and its concentration in the organic phase. Generally, it is preferred to extract the metal values from ammoniacal solutions in which the preferred concentration of ammonia is from about 10 to 150 g/l. However, it is understood that for each aqueous metal solution and sulfonamide reagent solution there will be a preferred or optimum set of extraction conditions, and those skilled in the art, based on the information given herein, especially in the examples to follow, will be able, after a limited number of trial runs, to determine such preferred or optimum conditions for the respective systems under consideration. This is equally true of the stripping operations. By the term stripping is meant the transfer of at least a portion of the metal values in the loaded organic phase to the aqueous stripping medium. The metal values so stripped are desirably recovered from the aqueous stripping medium by conventional techniques, preferably electrolysis. The volume ratios of loaded organic:aqueous stripping phase can also vary widely. However, the overall object of the process is to provide a metal containing stripping solution of known composition and concentration suitable for conventional recovery techniques such as electrolysis. Accordingly, the metal will preferably be present in higher concentrations in the aqueous stripping medium than in the starting metal containing solution. To accomplish this, the loaded organic:aqueous stripping medium phase ratio will normally be in the range of about 1:1 to 10:1. The stripping medium is preferably an aqueous mineral acid solution such as 25 to 250 g/l $H_2SO_4$.

While the process of the present invention has been described as particularly effective in extracting $Cu++$, $Ni++$, $Zn++$, $Co++$ and $Co+++$, metal values from aqueous solutions, it may also be applied to extract other chemically similar metal values, such as $Cd++$, $Hg++$, $Ag+$ and $Pb++$. The process of the invention thus provides a simple continuous method of extracting valuable metal values from aqueous solutions. Of equal importance is the economic advantages attendant from the process which allows the extracting reagent to be stripped of metal values and recycled for subsequent loading.

According to another embodiment of the invention, metal values can be selectively stripped from a loaded organic phase, i.e. an organic solution containing the metal complex of the heterocyclic sulfonamide compound, by sequential contacting with an acidic solution followed by an aqueous ammonia solution. For example, when a loaded organic phase contains both $Ni++$ and $Cu++$ metal values, the nickel is first stripped by contact with a dilute sulfuric acid solution and, subsequently, the copper can be recovered by contacting with an aqueous ammonia solution.

To further illustrate the various objects and advantages of the present invention, the following examples are provided. It is understood that their purpose is entirely illustrative and in no way intended to limit the scope of the invention.

EXAMPLE 1

Preparation of Starting Materials

A. Friedel-Crafts Alkylations

The alkylations were carried out via the procedure of Oleson (Ind. Eng. Chem., 52, 833 (1960)).

Approximately one-half to two-thirds of the starting aromatic hydrocarbon and the aluminum chloride were placed in a round bottom three-neck flask fitted with mechanical stirrer, addition funnel, thermocouple well or thermometer, and a condenser. A small portion of water (2 to 10 drops) was added. A solution of the olefin in the remainder of the aromatic hydrocarbon was added slowly with stirring to the reaction vessel. The reaction temperature was maintained somewhere in the range from 0° C. to 50° C. After addition was complete, the reaction mixture was stirred for an additional 15 to 20 minutes while the reaction temperature was maintained. A 10% hydrochloric acid solution (500 ml) was added and the mixture was stirred for 5 minutes. The phases were separated. The organic was washed twice with 2-5% sodium hydroxide, once with brine, and the excess aromatic was stripped off in vacuo. The product was fractionally distilled through a Vigreaux column under vacuum. The ratios of reactants, boiling points, and yields can be found in Table A.

TABLE A

| | | FRIEDEL-CRAFTS ALKYLATIONS | | | | | | |
|---|---|---|---|---|---|---|---|---|
| PRODUCT | RUN | AROMATIC HYDROCARBON | OLEFIN | AlCl₃ | REACTION TEMP °C. | BOILING POINT | | YIELD |
| | | | | | | mm of Hg | °C. | % |
| Decyltoluene | A | Toluene 5m | 1-Decene 1m | 0.05m | 40 | 0.45 | 95–100 | 67 |
| (Decylmethyl- | B | Toluene 10m | 1-Decene 1m | 0.025m | 0–5 | * | 150–155 | 79.9 |
| benzene) | C | Toluene 5m | 1-Decene 0.5m | 0.025m | 40 | 0.15 | 80–85 | 73 |
| | D | Toluene 71.4m | 1-Decene 7.6m | 0.357m | 40 | 0.55–0.8 | 106–124 | 76 |

*Water aspirator vacuum

B. Preparation of the Sulfonyl Chloride

The sulfonyl chlorides were prepared by two different routes starting from either the alkylbenzene or the alkylbenzenesulfonic acid.

Alkylbenzenesulfonyl chloride from the alkylbenzene

A solution of the alkylbenzene in 1,1,2-trichloroethane (TCE) was cooled to 10° C. and chlorosulfonic acid was added slowly with stirring. The pot temperature was maintained at 10°–15° C. during the addition. After the addition was complete, the reaction mixture was stirred at 10°–15° C. for 15 minutes and then allowed to warm to ambient temperature while stirring for 2–3 hours. The thionyl chloride was added to the stirring reaction mixture. The reaction mixture was heated slowly (1–3 hours) to 90°–120° C. and then held at 90°–120° C. for 30 minutes. A sample was then withdrawn from the reaction mixture. If the presence of the sulfonic acid anhydride was detected by IR, an additional mole of thionyl chloride was added and the reaction mixture was stirred at 90°–120° C. for one additional hour. The excess thionyl chloride and TCE were stripped from the reaction mixture in vacuo. The crude sulfonyl chloride was purified by molecular distillation.

Ratios of reactants, reaction temperatures, and yields are given in Table B.

TABLE B

PREPARATION OF ALKYLBENZENESULFONYL CHLORIDES FROM THE ALKYLBENZENE

| PRODUCT | RUN | ALKYL-BENZENE (m) | ClSO$_3$H (m) | SOCl$_2$ (m) | TCE (ml) | RXN TEMP °C. | DISTILLED YIELD (%) |
|---|---|---|---|---|---|---|---|
| Dodecylbenzenesulfonyl chloride | | 4.34 | 4.34 | 8.68 | 3.67 | 110 | 64 |
| Decyltoluenesulfonyl chloride | A | 5.87 | 5.87 | 11.74 | 500 | 120 | 67 |
| | B | 5.53 | 5.53 | 11.07 | 442 | 110 | 73 |
| | C | 0.25 | 0.275 | 0.55 | 10 | 116 | 56 |

Dodecylbenzenesulfonyl chlorides from the dodecylbenzenesulfonic acids

The sulfonic acid was added slowly over a four-hour period to a stirring solution of thionyl chloride (1 l.) in Skelly C (500 ml). The temperature controller was set for 95° C. and the reaction mixture was heated to reflux. The reaction mixture required approximately two hours to reach 95° C. After stirring at 95° C. overnight, the excess thionyl chloride and Skelly C were stripped off under aspirator vacuum. An additional 50 ml of Skelly C was added and then distilled off under aspirator vacuum to remove the last traces of thionyl chloride. The crude product was then purified by molecular distillation. Amounts of starting acid and yields are given in Table C.

TABLE C

CONVERSION OF SULFONIC ACIDS BY THIONYL CHLORIDE

| PRODUCT | ACID (m) | CRUDE % | DISTILLED (%) |
|---|---|---|---|
| Dodecylbenzenesulfonyl chloride | 5.82 | — | 94 |

C. Preparation of Amines

2-(2'-Aminophenyl)benzoxazole

Isatoic anhydride (0.2 m), o-anisidine (0.22 m), and xylene (200 ml) were placed in a 3-neck, 300 ml round bottom flask fitted with thermometer, condenser, and magnetic stirrer. The reaction mixture was heated to reflux and allowed to stir at reflux overnight. Gas evolution appeared to be vigorous. Added a Dean-Stark trap and attempted to collect water. No water was evident after eight hours. Reaction mixture was cooled and allowed to stand overnight. Toluenesulfonic acid (1.5 g) was added and reaction mixture heated to reflux. Water was azeotroped from the reaction mixture. The xylene was stripped from the reaction mixture under aspirator vacuum. The residue was leached with benzene (500 ml). The benzene extract was then washed with 2% caustic until no further color was extracted. The benzene solution was filtered and evaporated to dryness. The residue was dissolved in boiling ethanol and allowed to stand in the refrigerator. The reddish crystals were filtered out and dried. Obtained 10 grams (23% yield); m.pt.=104°–107° C. Structure was confirmed by infra red (IR) and nuclear magnetic resonance (NMR) analysis.

EXAMPLE 2

General Preparation of Sulfonamido Heterocyclic Compounds

The appropriate amine was dissolved in pyridine. The sulfonyl chloride was added slowly with stirring. During the addition, the reaction temperature was maintained at 15 to 30 degrees C. After the addition was complete, the reaction mixture was allowed to stir at room temperature from 30 minutes to several hours. The reaction mixture was then heated to 70 to 90 degrees C. and stirred from 30 minutes to 8 hours. Water (50 to 100 ml) was added and the reaction mixture was stirred at 70 to 80 degrees C. for 30 minutes. After pouring the reaction mixture into water (250 ml to 1500 ml), the product was recovered by extraction with an organic solvent; e.g. Skelly C, Skelly C/benzene, (50:50) or benzene. After extraction, the organic extract was washed with methanolic sodium bicarbonate and then with 1 to 5% mineral acid (sulfuric acid or hydrochloric acid). The methanolic bicarbonate washes were repeated until clean phase separations were obtained. The organic was then washed with brine, dried over sodium sulfate, filtered, and evaporated in vacuo. The resultant products were characterized by IR and NMR. The ratios of reactants, solvents, temperatures, and yields are given in Table D.

TABLE D

PREPARATION OF SULFONAMIDO HETEROCYCLES

| PRODUCT | AMINE (m) | SULFONYL CHLORIDE (m) | PYRIDINE (ml) | UPPER TEMPERATURE /HOLD TIME | EXTRACTION SOLVENT | YIELD (%) |
|---|---|---|---|---|---|---|
| 2-(Dodecylbenzenesulfonamido)pyridine | 1 | 1 | 500[1] | 90° C./2 hr | Skelly C | 83 |
| 2-(Dodecylbenzenesulfonamido)-6-methylpyridine | 0.1 | 0.11 | 200 | 90° C./4 hr | Skelly C | 93 |
| 2-(Dodecylbenzenesulfonamido)-6-hydroxypyridine | 0.1 | 0.1 | 200 | 90° C./4 hr | Skelly C | 96 |
| 3,5-Dichloro-2-(dodecylbenzenesulfonamido)pyridine | 0.1 | 0.11 | 50 | 90° C./7 hr | Skelly C | 85 |
| 2-(Dodecylbenzenesulfonamido)-3-nitropyridine | 0.1 | 0.17 | 30 | 90° C./96 hr | Benzene | 61 |
| 2-(Dodecylbenzenesulfonamido)-3-methylpyridine | 0.5 | 0.5 | 100[2] | 70° C./1 hr | Skelly C | 24 |
| 2-(Dodecylbenzenesulfonamido)-pyrimidine | 0.1 | 0.1 | 50 | 70° C./1 hr | Benzene | 37 |

TABLE D-continued

PREPARATION OF SULFONAMIDO HETEROCYCLES

| PRODUCT | AMINE (m) | SULFONYL CHLORIDE (m) | PYRIDINE (ml) | UPPER TEMPERATURE /HOLD TIME | EXTRACTION SOLVENT | YIELD (%) |
|---|---|---|---|---|---|---|
| 2-(Dodecylbenzenesulfonamido)-benzothiazole | 0.25 | 0.25 | 100 | 80° C./0.5 hr | Skelly C/Benzene | 100 |
| 3,4-Dimethyl-5-(dodecylbenzene-sulfonamido)isoxazole | 0.3 | 0.3 | 100 | 80° C./0.5 hr | Skelly C/Benzene | 74 |
| 2-(Dodecylbenzenesulfonamido)-5-methylisoxazole | 0.3 | 0.3 | 100 | 80° C./0.5 hr | Skelly C | 93 |

[1] Benzene (500 ml) was also present as reaction solvent.
[2] Toluene (200 ml) was also present as reaction solvent.

EXAMPLE 3

Preparation of 2-(dodecylbenzenesulfonamido)pyridine

Starting materials:
  94 gm (1 mole) 2-aminopyridine
  344 gm (1 mole) dodecylbenzenesulfonyl chloride
  500 ml pyridine
  500 ml benzene The sulfonyl chloride was added slowly with vigorous stirring to a solution of 2-aminopyridine in pyridine/benzene (1/1). The temperature was maintained between 25°–40° C. The reaction mixture was stirred at room temperature for approximately 16 hours. After stirring, the reaction mixture was heated to 90° C. and refluxed for 2 hours. One liter of water was added, the mixture was stirred for 3 hours and then allowed to cool to room temperature. The cooled mixture was poured into 1.5 liters of water to which one liter of Skelly C was added. The resulting phases were separated and allowed to stand overnight.

The organic phase was washed five times with one liter of 5% NaHCO$_3$ in an aqueous methanol solution (40% methanol, 60% water), one time with 5% HCl solution, one time with the 5% NaHCO$_3$ solution, one time with 500 ml brine, then dried over Na$_2$SO$_4$, filtered and evaporated to dryness in vacuo. 336.6 gm of a tan solid were obtained. NMR and IR analysis confirmed that the product was 2-(dodecylbenzenesulfonamido)pyridine.

EXAMPLE 4

Preparation of 2-(dodecylbenzenesulfonamido)-6-methylpyridine

Starting materials:
  10.8 gm (0.1 mole) 2-amino-6-methylpyridine
  37.8 gm (0.11) mole dodecylbenzenesulfonyl chloride
  200 ml pyridine The 2-amino-6-methylpyridine was dissolved in 200 ml of pyridine and the sulfonyl chloride was added slowly with stirring. After 30 minutes, the reaction mixture was heated to 90° C. and stirred for four hours. The reaction mixture was then poured into 1500 ml of water and extracted twice with 300 ml portions of Skelly C. The extract was washed three times with 500 ml of 5% NaHCO$_3$ in an aqueous methanol solution (40% methanol, 60% water), one time with 500 ml of 1% HCl, an additional time with the NaHCO$_3$ solution, one time with brine, then dried over Na$_2$SO$_4$, filtered and evaporated to dryness in vacuo. The product was placed under vacuum overnight to remove traces fo solvent. 39.7 gm (93%) of a yellow oil was obtained. NMR and IR analysis confirmed that the product was substantially 2-(dodecylbenzenesulfonamido)-6-methylpyridine.

EXAMPLE 5

Preparation of 3,5-dichloro-2-(dodecylbenzenesulfonamido)pyridine

Starting materials:
  16.2 gm (0.1 mole) 2-amino-3,5-dichloropyridine
  37.8 gm (0.11 mole) dodecylbenzenesulfonyl chloride
  50 ml pyridine The sulfonyl chloride was added slowly to the 2-amino-3,5-dichloropyridine in pyridine. The reaction mixture was heated to 90° C. and stirred for seven hours after which time the mixture was allowed to stand for approximately two days. The reaction mixture was then poured into 850 ml water and 200 ml Skelly C. The phases were allowed to separate and the organic phase was collected and washed four times with 200 ml of 5% NaHCO$_3$ in an aqueous methanol solution (40% methanol, 60% water), one time with a 5% HCl solution, one time with the 5% NaHCO$_3$ solution, one time with brine, then dried over Na$_2$SO$_4$ and evaporated to dryness after filtering. 40.7 gm of a thick viscous oil was obtained. NMR and IR analysis confirmed the structure of the compound to be 3,5-dichloro-2-(dodecylbenzenesulfonamido)pyridine, with small amounts of hydrocarbon impurity.

EXAMPLE 6

Preparation of 2-(dodecylbenzenesulfonamidomethyl)pyridine

Starting materials:
  22 gm (0.203 mole) 2-aminomethylpyridine
  66.4 gm (0.203 mole) dodecylbenzenesulfonyl chloride
  200 ml pyridine The sulfonyl chloride was added slowly to the 2-aminoethylpyridine and 200 ml of pyridine with stirring. The reaction mixture was stirred for two hours at room temperature and then heated to 70° C. and continuously stirred at 70° overnight. Thereafter, the reaction mixture was poured into 800 ml of H$_2$O and extracted by contacting three times with 250 ml of Skelly C. The Skelly C was washed twice with 500 ml of 5% NaHCO$_3$ in a 40% aqueous methanol solution, with brine, then dried over Na$_2$SO$_4$, decanted, heated to boiling, filtered and evaporated to dryness in vacuo. 77.1 gm of desired product was obtained. IR and NMR analysis confirmed the product to have the structure of 2-(dodecylbenzenesulfonamidomethyl)pyridine.

EXAMPLE 7

Preparation of 2-(p-methylbenzenesulfonamidomethyl)pyridine

Starting materials:

15.2 gm (0.15 mole) 2-aminomethylpyridine
32.3 gm (0.17 mole) p-methylbenzenesulfonyl chloride
150 ml pyridine The methylbenzenesulfonyl chloride was added slowly to a solution of the 2-aminomethylpyridine in pyridine. The reaction mixture was stirred at room temperature for approximately one hour and then stirred at 50° C. for one hour. 150 ml of water was added and the reaction mixture was again stirred at 50° C. for 15 minutes. The reaction mixture was poured into 500 ml of water and the resulting precipitate was filtered and recrystallized from 95% ethanol. Upon filtration from the ethanol solution, and drying, 30.8 gm of tan needles having a melting point of approximately 78°–80° C. were obtained. NMR and IR analysis confirmed the compound to be 2-(p-methylbenzenesulfonamidomethyl)pyridine.

EXAMPLE 8

Preparation of 2-(dodecylbenzenesulfonamido)pyrimidine

Starting materials:
9.5 gm (0.1 mole) 2-aminopyrimidine
34.4 gm (0.1 mole) dodecylbenzenesulfonyl chloride
50 ml pyridine Sulfonyl chloride was added slowly with stirring to a solution of 2-aminopyrimidine in pyridine at room temperature. After three hours, the reaction mixture was heated to 70° C. and stirred for an additional hour. The reaction mixture was poured into 800 ml of water and extracted with benzene. The resulting emulsion was allowed to settle overnight. The reaction mixture was repeatedly extracted with 5% NaHCO$_3$ in a 40% aqueous methanol solution until separation was complete. The extract was washed with brine, dried over Na$_2$SO$_4$, filtered and evaporated to dryness in vacuo. 14.9 gm (37%) of a yellow substance was obtained. NMR and IR analysis confirmed that the substance was a compound having the structure of 2-(dodecylbenzenesulfonamido)pyrimidine.

EXAMPLE 9

Preparation of 2-(decylmethylbenzenesulfonamido)pyrimidine

Starting materials:
19 gm (0.2 mole) 2-aminopyrimidine
66 gm (0.2 mole) decylmethylbenzenesulfonyl chloride
50 ml pyridine A solution of the 2-aminopyrimidine in pyridine was heated to 50° C. with continuous stirring. The decylmethylbenzenesulfonyl chloride was added slowly over a period of 30 minutes. The reaction mixture was then heated to 80° C. and stirred overnight. Thereafter, 20 ml of water was added and the mixture was again stirred at 50° C. for two hours, cooled, and allowed to stand for approximately two days. The mixture was then poured into a solution of 30 ml toluene, 20 ml Skelly C and 50 ml H$_2$O. The mixture was shaken, heated and allowed to settle. Phases were separated and the organic phase was extracted with 6% aqueous ammonia. The organic phase was washed with a sulfuric acid solution (50 gm per liter) and the resulting phases were separated. The organic phase was dried over Na$_2$SO$_4$, filtered and evaporated to give a dark oil. The aqueous ammonia solution was neutralized to a pH of 2 with dilute sulfuric acid and extracted with toluene so as to obtain an organic phase which was stripped to obtain the product as previously described. 50.3 gm of a white solid were obtained in total. NMR and IR analysis confirmed the structure of the compound to be 2-(decylmethylbenzenesulfonamido)pyrimidine.

EXAMPLE 10

Preparation of 2-(dodecylbenzenesulfonamido)benzothiazole

Starting materials:
37.5 gm (0.25 mole) 2-aminobenzothiazole
86 gm (0.25 mole) dodecylbenzenesulfonyl chloride
100 ml pyridine The sulfonyl chloride was added slowly to a solution of the 2-aminobenzothiazole in pyridine at 15° C. with stirring. The mixture was allowed to stand overnight. Thereafter, it was heated to 80° C. for 30 minutes after which 50 ml of water was added. The mixture was then poured into one liter of water and one liter of hexane. The phases were separated and the organic phase was washed with 50 ml of 6% ammonia solution. A precipitate formed which was dissolved back into the organic phase by addition of one liter of benzene. The organic phase was then washed twice with 2% NaHCO$_3$ in an aqueous methanol solution (20% methanol), twice with 75 gm per liter H$_2$SO$_4$, once with brine, then dried over Na$_2$SO$_4$, filtered and evaporated in vacuo. 127.5 gm of a waxy solid were obtained. NMR and IR analysis confirmed the product to be 2-(dodecylbenzenesulfonamido)benzothiazole.

EXAMPLE 11

Preparation of 3-(dodecylbenzenesulfonamido)-5-methylisoxazole

Starting materials:
25.4 gm (0.3 mole) 3-amino-5-methylisoxazole
103 gm (0.3 mole) dodecylbenzenesulfonyl chloride
100 ml pyridine The sulfonyl chloride was slowly added to a solution of the isoxazole in pyridine with continuous stirring at 15°–20° C. Stirring was continued overnight at room temperature. Thereafter, the reaction mixture was heated to 80° C. for approximately ½ hour and 50 ml of water was added and stirred for 30 minutes. The mixture was poured into 50 ml of Skelly C and 250 ml of water and the phases were separated. The organic phase was washed twice with 2% NaHCO$_3$ in a 20% aqueous methanol solution, twice with 50 gm per liter H$_2$SO$_4$, once with the 2% NaHCO$_3$ solution, once with brine, then dried over Na$_2$SO$_4$ and filtered. 112.6 gm of a dark oil was obtained. NMR and IR analysis confirmed the product to be 3-(dodecylbenzenesulfonamido)-5-methylisoxazole.

EXAMPLE 12

Preparation of 3,4-dimethyl-5-(dodecylbenzenesulfonamido)isoxazole

Starting materials:
33.6 gm (0.3 mole) 5-amino-3,4-dimethylisoxazole
103 gm (0.3 mole) dodecylbenzenesulfonyl chloride
100 ml pyridine The synthesis was the same as that described in Example 19. 90.5 gm of an oil were obtained. NMR and IR analysis indicated the product to have the structure of 3,4-dimethyl-5-(dodecylbenzenesulfonamido)isoxazole although there were some aromatic and aliphatic impurities.

EXAMPLE 13

Preparation of 2-(2'-[decylmethylbenzenesulfonamido]phenyl) benzoxazole

Starting materials:
 10 gm (0.0476 mole) benzoxazole of Example 1. C.
 16.5 gm (0.05 mole) decylmethylbenzenesulfonyl chloride
 50 ml pyridine The decylmethylbenzenesulfonyl chloride was slowly added to a solution of benzoxazole in pyridine and stirred at room temperature for 6 hours. Thereafter, the reaction mixture was heated to 80° C. and stirred for 8 hours, cooled and allowed to stand overnight. The mixture was then heated to reflux and stirred for 8 hours, cooled and again allowed to stand overnight. The mixture was then heated a second time to 80° C., poured into 250 ml of water and 250 ml of Skelly C. The resulting phases were separated. The organic phase was washed three times with a 6% aqueous ammonia solution and three times with 50 gm per liter of $H_2SO_4$. The washed organic phase was dried over $Na_2SO_4$, filtered and evaporated in vacuo. 14.8 gm of an oil which solidified upon standing were obtained. NMR and IR analysis confirmed the product to be 2-(2'-[decylmethylbenzenesulfonamido]phenyl)benzoxazole.

EXAMPLE 14

Extraction of Metal Values

To determine the ability of the various heterocyclic sulfonamide compounds of the present invention to extract metal values from aqueous solutions, tests were conducted in accordance with the following procedures in the Extraction of $Cu^{++}$, $Ni^{++}$, $Zn^{++}$, $Co^{++}$ and $Co^{+++}$.

A 0.1 molar solution of the sulfonamide compound in an identified essentially water-immiscible liquid hydrocarbon solvent and five aqueous solutions of the following compositions were used:

| Metal | Composition |
| --- | --- |
| $Cu^{++}$ | 0.05 M $CuSO_4$ (3.2 g./l. $Cu^{++}$), 0.4 M $NH_3$, and 0.1 M $(NH_4)_2SO_4$ |
| $Ni^{++}$ | 0.05 M $NiSO_4$ (2.9 g./l. $Ni^{++}$), 0.4 M $NH_3$, and 0.1 M $(NH_4)_2SO_4$ |
| $Zn^{++}$ | 0.05 M $ZnSO_4$ (3.2 g./l. $Zn^{++}$), 0.4 M $NH_3$, and 0.1 M $(NH_4)_2SO_4$ |
| $Co^{++}$ | 0.025 M $CoSO_4$ (1.5 g./l. $Co^{30 +}$), 1.7 M $NH_3$, and 0.1 M $(NH_4)_2SO_4$ prepared as needed under an atmosphere of nitrogen |
| $Co^{+++}$ | 0.025 M $CoSO_4$ (1.5 g./l. $Co^{30 +}$), 1.7 M $NH_3$, and 0.1 M $(NH_4)_2CO_3$ (air oxidized to $Co^{+++}$) |

Portions of the organic solution were shaken with the five aqueous solutions at an organic:aqueous phase volume ratio of 1:1 for one hour at ambient temperature. The organic phases were then analyzed for metal content. If a third phase was present, both the organic and aqueous phases were clarified and analyzed. Table E summarizes the data obtained from the extraction tests for various heterocyclic sulfonamide reagents of the present invention.

TABLE E

| REAGENT | SOLVENT | $[Cu^{+2}]$ ORG. | $[Ni^{+2}]$ ORG. | $[Co^{+2}]$ ORG. | $[Co^{+3}]$ ORG. | $[Zn^{+2}]$ ORG. |
| --- | --- | --- | --- | --- | --- | --- |
| 2-(Dodecylbenzenesulfonamido)-pyridine | Exxon Aromatic 150 | 1.56 | 1.84 | — | 0.023 | 1.15 |
| 2-(Dodecylbenzenesulfonamido)-6-methylpyridine | Exxon Aromatic 150 | 1.73 | 2.06 | 1.24 | 0.048 | 1.72 |
| 3,5-Dichloro-2-(dodecylbenzenesulfonamido)pyridine | Exxon Aromatic 150 | 0.534 | 0.880 | 0.009* | 0.647 | 0.575 |
| 2-(Dodecylbenzenesulfonamidomethyl)pyridine | Exxon Aromatic 150 | 2.37 | 1.40 | — | 0.011 | 0.78 |
| 2-(Methylbenzenesulfonamidomethyl)pyridine | 1,1,2-Trichloroethane | 2.87 | 2.05 | — | — | 1.16 |
| 2-(Dodecylbenzenesulfonamido)-pyrimidine | KerMac 470B | 2.28 | 2.13 | 0.865 | 1.00 | 2.32 |
| 2-(Dodecylbenzenesulfonamido)-benzothiazole | Exxon Aromatic 150 | 1.50 | 1.18 | 1.17 | 1.09 | 2.37 |
| 3,4-Dimethyl-5-(dodecylbenzenesulfonamido)isoxazole | Exxon Aromatic 150 | 1.34 | 0.010 | 0.125 | 1.03 | 1.50 |
| 2-(Dodecylbenzenesulfonamido)-5-methylisoxazole | Exxon Aromatic 150 | 2.14 | 2.45 | 1.17 | 1.17 | 2.81 |
| 2-[2'-(Decylmethylbenzenesulfonamido)phenyl]benzooxazole* | Exxon Aromatic 150 | 1.8 | 2.1 | 1.32 | 0.00 | 1.97 |

All concentrations are in grams per liter.
*Precipitate present

EXAMPLE 15

Ammonia Isotherms

To determine the extent of extraction of various metal ions as a function of total ammonia concentration in the aqueous phase, tests were conducted in accordance with the following procedure. Portions of a 0.1 molar solution of a heterocyclic sulfonamide compound in an identified essentially water-immiscible liquid hydrocarbon solvent were shaken at a 1:1 organic:aqueous phase ratio for one hour at ambient temperature with aqueous solutions made up as follows:

| Aqueous Solution | Metal Sulfate Concentration | $NH_3$ Concentration | $(NH_4)_2SO_4$ Concentration | Total $NH_3$ Concentration |
| --- | --- | --- | --- | --- |
| 1 | 0.005M | 0.60M | 0.15M | 0.90M(15.3 gpl) |
| 2 | 0.005M | 1.20M | 0.30M | 1.80M(30.6 gpl) |
| 3 | 0.005M | 2.40M | 0.60M | 3.60M(61.2 gpl) |

-continued

| Aqueous Solution | Metal Sulfate Concentration | $NH_3$ Concentration | $(NH_4)_2SO_4$ Concentration | Total $NH_3$ Concentration |
|---|---|---|---|---|
| 4 | 0.005M | 3.60M | 0.90M | 5.40M(91.8 gpl) |
| 5 | 0.005M | 4.80M | 1.20M | 7.20M(122.4 gpl) |
| 6 | 0.005M | 6.00M | 1.50M | 9.00M(1.53.0 gpl) |

(A convenient procedure for the preparation of the aqueous solutions involves the preparation of a large batch of solution 6. That solution then is diluted with an appropriate amount of a 0.005 M metal sulfate solution. For example, one liter of aqueous $CuSO_4$ solution 4 can be prepared by diluting 600 ml. of aqueous $CuSO_4$ solution 6 to one liter with 0.005 M $CuSO_4$ in water.)

The separated organic and aqueous phases were analyzed for metal concentration generating the data contained in Table F-J which demonstrates the degree of metal extraction as a function of ammonia concentration for the particular reagent systems under study. In the table concentrations are given in grams per liter unless other indicated.

EXAMPLE 16

Acid Stripping, Ammonia Loading and Acid Loading

In order to determine (1) the extent of metal stripping as a function of acid concentration, (2) the extent of ammonia loading during extraction and (3) the extent of acid loading during stripping, the following tests were conducted. Organic reagent solutions as used in Examples 22–24 and aqueous solutions having the following compositions were prepared:

A. a 0.1 M metal sulfate, 0.6 M $NH_3$ and 0.15 M $(NH_4)_2SO_4$ solution in water.

B. Four solutions containing 25, 50, 100 and 150 gpl $H_2SO_4$ in water.

In the first step, the sulfonamide solution was shaken with aqueous solution A at an organic:aqueous phase volume ratio of 1:2 for one hour at ambient temperature. The phases were separated and the loaded organic phase was contacted a second time as before with fresh aqueous solution A. The resulting organic phase was separated and analyzed for metal concentration. The loaded organic phase was then divided into four parts each of which is shaken with one of the four aqueous B solutions at an organic:aqueous phase ratio of 1:1 for one hour at ambient temperature. The phases were then separated and the organics were analyzed for metal content while the aqueous phases were analyzed for ammonia concentration. Next, the stripped organic phases were washed with water at an organic:aqueous phase ratio of 1:1 for one hour and analyzed for $H_2SO_4$ concentration. The results of this procedure are disclosed in Table K.

EXAMPLE 17

Selective Stripping of $Cu^{++}$ and $Ni^{++}$ from 2-(dodecylbenzenesulfonamido)pyridine By correct selection of acidic stripping conditions, e.g. pH control, it is possible to selectively strip nickel values from a loaded organic phase without removing any copper. The copper may be quantitatively removed by contacting the organic phase with an aqueous solution of ammonia. Table L provides data for the selective removal of nickel and copper from a loaded 2-(Dodecylbenzenesulfonamido)pyridine reagent solution. The loaded organic phase was prepared by contacting a 0.1 molar solution of 2-(Dodecylbenzenesulfonamido)pyridine in Solvesso 150 with an aqueous solution containing 0.025 M $Cu^{++}$, 0.025 M $Ni^{++}$, 0.4 M $NH_3$ and 0.1 M $(NH_4)_2SO_4$ for one hour.

Table F

| 2-(Dodecylbenzenesulfonamido)-6-methylpyridine | | | | | | | |
|---|---|---|---|---|---|---|---|
| [$NH_3$] Extracted [$NH_3$] | % Cu Extracted | [$NH_3$]Extracted | % Ni Extracted | [$NH_3$] | % Co Extracted | [$NH_3$] | % Zn Extracted |
| 14.8 | 74 | 15.1 | 85.6 | 14.7 | 9.5 | 14.4 | 62.1 |
| 30.0 | 28.5 | 30.0 | 77.9 | 29.7 | 2.4 | 28.9 | 27.7 |
| 60.0 | 6.3 | 60.0 | 43.2 | 56.7 | 2.7 | 58.3 | 12.4 |
| 86 | 2.6 | 89.5 | 17.1 | 77.6 | 3.2 | 87.2 | 6.7 |
| 114 | 1.6 | 118.6 | 6.6 | 102.6 | 3.9 | 116.2 | 4.9 |
| 142 | 1.2 | 149.6 | 3.2 | 129.2 | 5.6 | 147.0 | 4.2 |

Table G

| 3,5-Dichloro-2-(dodecylbenzenesulfonamido)pyridine in Exxon Aromatic 150 | | | | | | | |
|---|---|---|---|---|---|---|---|
| [$NH_3$] | % Cu Extracted | [$NH_3$] | % Ni Extracted | [$NH_3$] | % Co Extracted | [$NH_3$] | % Zn Extracted |
| 15.0 | 75.6 | 15.13 | 47.5 | 14.8 | 26.5* | 14.4 | 62 |
| 29.9 | 46.5 | 29.4 | 25.9 | 29.7 | 49.2 | 28.9 | 34.4 |
| 55.4 | 20.6 | 60.1 | 4.0 | 56.8 | 20.5 | 58.3 | 11.7 |
| 85.1 | 10.9 | 89.9 | 2.8 | 77.7 | 12.9 | 87.2 | 12.3 |
| 104.0 | 8.1 | 119 | 1.5 | 102.7 | 13.5 | 116.2 | 4.1 |
| 134.0 | 7.5 | 145 | 0.0 | 130.2 | 2.7 | 147.0 | 3.2 |

*Precipitate present.

TABLE H

| 2-(Decylmethylbenzenesulfonamido)pyrimidine in Toluene | | | | | | | |
|---|---|---|---|---|---|---|---|
| [$NH_3$] | % Cu Extracted | [$NH_3$] | % Ni Extracted | [$NH_3$] | % Co Extracted | [$NH_3$] | % Zn Extracted |
| 15.3 | 83.3 | 15.1 | 56.7 | 15.3 | 90.6 | 14.4 | 39.3 |
| 30.6 | 73.6 | 30.0 | 31.1 | 30.6 | 94.2 | 28.9 | 19.2 |

TABLE H-continued

| 2-(Decylmethylbenzenesulfonamido)pyrimidine in Toluene | | | | | | | |
|---|---|---|---|---|---|---|---|
| $[NH_3]$ | % Cu Extracted | $[NH_3]$ | % Ni Extracted | $[NH_3]$ | % Co Extracted | $[NH_3]$ | % Zn Extracted |
| 61.2 | 90.0 | 60.0 | 31.1 | 61.2 | 92.0 | 58.3 | 12.9 |
| 91.8 | 56.0 | 89.5 | 18.7 | 91.8 | 88.4 | 87.2 | 0.0 |
| 122.4 | 42.3 | 118.6 | 20.6 | 122.4 | 81.8 | 116.2 | — |
| 153.0 | 29.0 | 149.6 | — | 153.0 | 75.5 | 147.0 | |

Emulsions were encountered throughout these tests.

TABLE I

| 2-(Dodecylbenzenesulfonamido)benzothiazole in Exxon Aromatic 150 | | | | | | | |
|---|---|---|---|---|---|---|---|
| $[NH_3]$ | % Cu Extracted | $[NH_3]$ | % Ni Extracted | $[NH_3]$ | % Co Extracted | $[NH_3]$ | % Zn Extracted |
| 15.1 | 97.4 | 15.1 | 66.0 | 14.7 | 75.0 | 14.4 | 86.3 |
| 29.9 | 81.6 | 30.0 | 57.6 | 29.7 | 76.0 | 28.9 | 89.7 |
| 55.4 | 52.2 | 60.0 | 33.4 | 56.7 | 70.0 | 58.3 | 56.6 |
| 85.1 | 30.8 | 89.5 | 21.1 | 77.6 | 54.6 | 87.2 | 30.4 |
| 104.0 | 20.0 | 118.6 | 13.2 | 102.6 | 38.8 | 116.2 | 21.1 |
| 141.9 | 12.2 | 149.6 | 10.7 | 129.2 | 32.3 | 147.0 | 11.4 |

TABLE J

| 2-(Dodecylbenzenesulfonamido)-5-methylisoxazole in Exxon Aromatic 150 | | | | | | | |
|---|---|---|---|---|---|---|---|
| $[NH_3]$ | % Cu Extracted | $[NH_3]$ | % Ni Extracted | $[NH_3]$ | % Co Extracted | $[NH_3]$ | % Zn Extracted |
| 15.1 | 93.3 | 15.1 | 79.5 | 14.7 | 74.8 | 14.4 | 96.3 |
| 29.9 | 79.7 | 30.0 | 74.3 | 29.7 | 71.9 | 28.9 | 87.8 |
| 55.4 | 51.5 | 60.0 | 46.5 | 56.7 | 58.3 | 58.3 | 57.2 |
| 85.1 | 32.1 | 89.5 | 28.7 | 77.6 | 42.5 | 87.2 | 35.5 |
| 104.0 | 24.0 | 118.6 | 20.1 | 102.6 | 29.4 | 116.2 | 22.0 |
| 141.9 | 14.8 | 149.6 | 16.3 | 129.2 | 21.8 | 147.0 | 15.4 |

TABLE K

| 0.1 REAGENT | Metal | $[H_2SO_4]$ Strip | [M] Org. Feed | [M] Org. Raffinate | $[NH_3]$ Strip Raffinate | $[H^+]$ Water Wash |
|---|---|---|---|---|---|---|
| 2-(Dodecylbenzenesulfonamido)-pyridine | Cu | 75 | 2.43 | 1.90 | 0.119 | <0.098 |
| | Cu | 150 | 2.43 | 1.85 | 0.102 | <0.098 |
| | Ni | 25 | 2.43 | 0.0018 | 0.85 | <0.098 |
| | Zn | 25 | 0.990 | 0.0015 | 1.36 | <0.098 |
| 2-(Dodecylbenzenesulfonamido)-6-methylpyridine | Zn | 25 | 1.66 | <0.0005 | 0.85 | pH = 6.5 |
| | Zn | 150 | 1.66 | <0.0005 | 0.85 | pH = 2.5 |
| 2-(Dodecylbenzenesulfonamido)-pyrimidine | Co | 25 | 0.288 | 0.0194 | 0.255 | pH = 6.8 |
| | Co | 150 | 0.288 | 0.056 | 0.17 | pH = 6.3 |

All concentrations are given in grams per liter.

TABLE L

| SELECTIVE STRIPPING OF COPPER (II) AND NICKEL (II) FROM 2-(DODECYLBENZENESULFONAMIDO)PYRIDINE, 1 | | | | |
|---|---|---|---|---|
| O/A | FEED | AQUEOUS FEED | PHASE | Cu | Ni |
| 1/1 | Fresh Org. | $H_2O$ | Org. 1 | 0.431 | 0.820 |
| | | | Aq. 1 | <0.0005 | <0.0005 |
| 1/1 | Fresh Org. | 10 gpl $H_2SO_4$ | Org. 2 | 0.302 | <0.0005 |
| | | | Aq. 2 | 0.127 | 1.08 |
| 1/1 | Org. 1 | 20 gpl $Ni^{+2}$/pH2 | Org. 3 | 0.439 | 0.0515 |
| | | | Aq. 3 | <0.0005 | 27.8*** |
| 1/1 | Org. 3 | 0.005M $Cu^{+2}$/30 gpl $NH_3$ | Org. 4 | 0.0118 | 0.0045 |
| | | | Aq. 4 | 0.720 | 0.0725 |

Concentrations are in grams per liter.
***The accuracy of the analytical method at this concentration is questionable.

While the invention has now been described in terms of various preferred process parameters, and exemplified with respect thereto, the skilled artisan will appreciate that various substitutions, changes, omissions, and modifications may be made without departing from the spirit thereof. Accordingly, it is intended that the scope of the invention be limited solely by that of the following claims.

The embodiments of the invention in which an exclusive property or privilege is claimed are defined as follows:

1. Compounds of the structure:

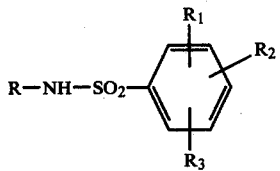

wherein R is a pyridine group of the structure:

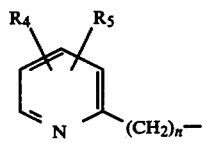

wherein $R_4$ and $R_5$, which may be the same or different, are selected from the group consisting of hydrogen, linear and branched chain alkyl and alkenyl containing from 1 to 20 carbon atoms, halogen, nitrile, alkoxy containing from 1 to 20 carbon atoms, and trifluoromethyl and n is an integer equal to 0 or 1, said pyridine group being bonded to the sulfonamido group through a carbon adjacent to the hetero atom of the ring and $R_1$, $R_2$ and $R_3$, which may be the same or different, are selected from the group consisting of hydrogen, and linear and branched chain alkyl and alkenyl containing from 1 to 20 carbon atoms, said compounds being further characterized as having solubilities of at least 2% by weight in essentially water-immiscible liquid hydrocarbon solvents.

2. The compounds of claim 1, wherein the sum of the carbon atoms in the alkyl and alkenyl groups is at least 8.

3. The compounds of claim 2, wherein at least one of $R_1$, $R_2$, and $R_3$ is alkyl or alkenyl containing at least 8 carbon atoms.

4. The compounds of claim 3, wherein said alkyl or alkenyl is branched chain.

5. The compounds of claim 1, wherein one of $R_1$, $R_2$ and $R_3$ is dodecyl.

6. The compounds of claim 1, wherein $R_4$ and $R_5$ are each hydrogen.

7. The compounds of claim 1, wherein one of $R_4$ and $R_5$ is methyl.

8. The compounds of claim 1, wherein at least one of $R_4$ and $R_5$ is halogen.

9. The compounds of claim 8, wherein said halogen is chloro.

10. The compounds of claim 1, wherein one of $R_1$, $R_2$ and $R_3$ is dodecyl.

11. The compounds of claim 1, wherein one of $R_1$, $R_2$ and $R_3$ is methyl.

12. The compounds of claim 10, wherein n is 1.

13. The compounds of claim 11, wherein $R_4$ and $R_5$ are each hydrogen.

14. 2-(Dodecylbenzenesulfonamido)pyridine.

15. 2-(Dodecylbenzenesulfonamido)-6-methylpyridine.

16. 3,5-Dichloro-2-(dodecylbenzenesulfonamido)-pyridine.

17. 2-(Dodecylbenzenesulfonamido)-3-nitropyridine.

18. 2-(Dodecylbenzenesulfonamido)-3-methylpyridine.

19. 2-(Dodecylbenzenesulfonamidomethyl)pyridine.

* * * * *